US00PP09048P

United States Patent [19]

Olesen et al.

[11] Patent Number: Plant 9,048

[45] Date of Patent: Jan. 31, 1995

[54] MINIATURE ROSE PLANT NAMED POULTOP

[75] Inventors: Mogens Olesen; Pernille Olesen, both of Fredensborg, Denmark

[73] Assignee: Weeks Wholesale Rose Grower, Inc., Upland, Calif.

[21] Appl. No.: 177,541

[22] Filed: Jan. 5, 1994

[51] Int. Cl.[6] ..... A01H 5/00

[52] U.S. Cl. ..... Plt./10

[58] Field of Search ..... Plt. 9, 10, 10.1, 27, Plt. 28

*Primary Examiner*—Howard J. Locker

*Attorney, Agent, or Firm*—Christie, Parker & Hale

[57] ABSTRACT

A new variety of miniature rose suitable for garden decoration, having flowers of brilliant orange red coloration.

1 Drawing Sheet

BACKGROUND OF THE INVENTION

This invention relates to a new and distinct variety of miniature rose. The varietal denomination of the new variety is 'Poultop'. The plant is a dwarf bushy seedling cultivated for outdoor garden decoration. It has as its seed parent an unnamed seedling and as its pollen parent an unnamed seedling.

SUMMARY OF THE INVENTION

Among the features which distinguish the new variety 'Poultop' from other presently available and known commercial rose cultivars are the following combination of characteristics: its well-formed flowers of brilliant orange red color, its dark glossy foliage, its fragrance carried on the stipitate glands on the outside of the bud and its abundant flower production on a very compact habit. 'Poultop' may be asexually propagated by cuttings, budding, grafting, layering and tissue culture.

Asexual reproduction of the new variety as performed by budding in Kern County and Upland, Calif., shows that the foregoing and other distinguishing characteristics come true to form and are established and transmitted through succeeding propagations.

COMPARISON WITH PARENT VARIETIES

The new rose may be distinguished from its seed parent, an unnamed seedling, by the following combination of characteristics: whereas the seed parent bears flowers of a deep red coloration, 'Poultop' bears flowers of a bright orange red coloration. The new cultivar is classified as a Miniature with proportionately smaller flowers and foliage, whereas the seed parent is classified as a Floribunda with significantly larger flowers and foliage.

The new variety may be distinguished from its pollen parent, an unnamed seedling, by the following combination of characteristics: 'Poultop' bears bright orange red flowers with 18 to 22 petals, whereas the pollen parent bears significantly lighter coral orange flowers of lower petalage. The pollen parent has small foliage of a light green coloration, whereas the new cultivar has significantly larger foliage of much darker green color.

BRIEF DESCRIPTION OF THE ILLUSTRATION

The accompanying photograph illustrates the plant in color and shows the flowering thereof from bud to full bloom depicted in color as nearly correct as it is possible to make in a color illustration of the character. Throughout this specification, color values are in accordance with The Colour Chart of The Royal Horticultural Society of London, England, except where common terms of color definition are employed.

DESCRIPTION OF THE NEW VARIETY

The following description is of rose plants of the new cultivar grown outdoors in Upland, Calif. in the month of Aug. Phenotypic expression may vary with environmental, cultural and climatic conditions, as well as differences in conditions of light and soil.

FLOWER

The new variety bears its flowers sometimes singly, usually four to five or more per stem. Flowers are borne in irregular rounded clusters on normally storng, medium to long stems for the class. Outdoors the plant blooms abundantly and nearly continuously during the growing season. The flowers have no fragrance.

BUD

The peduncle is of average to long length for the class, of average to heavy caliper, and usually erect. It is moderately rough with numerous stipitate glands and some hairs. Peduncle color is between 138A and 144A sometimes blushed with near 183A. The peduncle is considered as average to long for the class and nominally about 3 to 4 cm. Bud size is considered medium in size and length measuring, nominally, about 1.5 to 2 cm. in length and about 2.5 to 3 cm. in diameter at the widest point.

Before the calyx breaks, the bud is of medium size for the class, medium in length, and slightly pointed to mostly ovoid in shape. The surface of the bud bears few foliaceous appendages and several stipitate glands usually with slender foliaceous parts extending beyond the tip of the bud equal to one-fourth or more of its length. Bud color is between 144A and 138A sometimes blushed with near 183A. The stipitate glands on the surface of the bud bear the fragrance of moss rose because of moss roses in the ancestry of the new variety.

The inner surface of the sepals is covered and edged with fine wooly tomentum; sepal margins are lined with some stipitate glands and hairs.

As the petals open, the bud is medium sized for the class, medium in length, and pointed to ovoid in form. The color of the outside and inside surfaces of the newly opened petals is between 42A and 45C with a very small basal attachment zone of near 154D. The bud does open up well and is generally not prevented from opening by wet, cold, hot or dry weather.

BLOOM

When fully open, the bloom is moderately large for the class, ranging from 4 to 6 cm. in diameter. Petalage is double with 18 to 22 petals and 1 to 3 petaloids arranged regularly. When partially open, the bloom form is high centered and the petals are somewhat spiraled to cupped with petal edges moderately rolled outward. When fully open, the bloom form is cupped and the petals are undulated with petal edges somewhat rolled outward.

PETALS

The petals are of moderately heavy substance and of medium thickness, with inside surfaces slightly satiny to velvety and outside surfaces somewhat shiny to satiny. The outer petals are nearly round to broadly obovate in shape with apices rounded. The inside petals are somewhat broadly obovate in shape with apices usually rounded to slightly flat.

NEWLY OPENED FLOWER

The outside and inside surface of the outer, intermediate and inner petals is between 42A and 46D with a very small basal attachment zone of near 1D. A small halo of near 55B surrounds the basal attachment zone.

The general tonality of the newly opened flower is between 42A and 46D.

THREE-DAY-OLD FLOWER

The outside surface of the outer and inner petals is between 45D and 47C with a small basal attachment zone of near 4D. The inside surface of the outer and inner petals is between 42A and 47B with a basal attachment zone of similar size and coloration. A moderately sized halo of near 55C surrounds the basal attachment zone.

The general tonality of the three day old flower is between 42A and 47B.

On the spent bloom, the petals usually drop off cleanly and are not particularly affected by cold, hot, wet or dry weather.

In August, blooms on the bush grown outdoors gnerally last from three to four or more days. Cut roses from plants grown outdoors and kept at normal indoor living temperatures generally last from four to five days.

MALE REPRODUCTIVE ORGANS

Stamens are average to many in number and are arranged regularly about the pistil. The filaments are of somewhat medium to uneven length, most with anthers. The anthers are somewhat small to medium for the class and all open approximately at the same time. Anther color is near 21A when immature and near 166A at maturity. Pollen is somewhat sparse and near 15C in color.

FEMALE REPRODUCTIVE ORGANS

Pitstils are average in number (approximately 45). The styles are moderately uneven, short to average in length, average in caliper, and moderately bunched. Stigma color is near 154C. Style color is near 42B. Ovaries are usually allen closed in the calyx.

Hips are of moderately short length, somewhat globular in form, and near 33B in color. The hip surface is moderately smooth with very thick fleshy walls. The sepals fall quickly. Seeds are average in number for the class (approximately 8 to 15), and somewhat small to medium in size.

FOLIAGE

The compound leaves are usually comprised of three to five or more leaflets and are borne in normal quantities. The leaves are somewhat large for the class, moderately heavy in texture, and somewhat semi-glossy in finish. The leaflets are shaped somewhat round to broadly oval with somewhat acute to slightly mucronate apices and moderately round bases. Their margins are simply serrate to irregular. The foliage is considered somewhat large for the class with full leaf measuring nominally about 6.5 to 7 cm. in length and about 4 to 5.5 cm. in width and the widest point. Individual leaflets are nominally about 2.5 to 3 cm. in length and about 1.5 to 2 cm. in width of the widest point. The stem length is typically medium to long, measuring about 7 to 13 cm. in length.

The upper surface of the mature leaf is between 137A and 147A. The under surface of the mature leaf is near 191B. The upper surface of the young leaf is between 137A and 147A, usually heavily suffused with between 183A and 187A. The under surface of the young leaf is between 183C and 183D.

The rachis is average in caliper and moderately smooth with few stipitate glands on the edges of the upper side. The under side of the rachis is very smooth with few stipitate glands.

The stipules are moderately long in length with medium width medium length straigh points that usually turn out at an angle of more than 45 degrees.

The plant displays an average degree of resistance to powdery mildew and blackspot as compared to other commercial varieties grown under comparable conditions in Upland, Calif.

GROWTH

The plant has a dwarf, bushy, compact, medium height habit with moderately full branching. It displays vigorous growth and the canes are of moderately heavy caliper for the class. Mature plants attain a height and breath, both, of about 40 to 60 cm.

The color of the major stems are between 138B and 146C. They bear few large prickles which are somewhat medium length to long for the class. The large prickles are almost straight angled slightly downward with a medium length moderately narrow base; prickle color is near 166C. The major stems bear few small prickles of similar coloration and shape. There are no coarse hairs.

The color of the branches is between 138A and 144A. They bear few large prickles and many smaller prickles of various sizes which are medium length to long for the class. The prickles are almost straight angled slightly downward with a medium length moderately narrow base and prickle color is near 171B. There are some coarse hairs of similar coloration.

The color of the new shoots is between 138B and 144B often lightly suffused with near 183C. They bear several large prickles and many small prickles of various sizes which are medium to long for the class. The prickles are almost straight, angled slightly downward with a medium length moderately narrow base; prickle color is near 183B. The shoots bear many coarse hairs of similar coloration.

We claim:

1. A new and distinct variety of miniature rose plant substantially as described and illustrated herein.

* * * * *

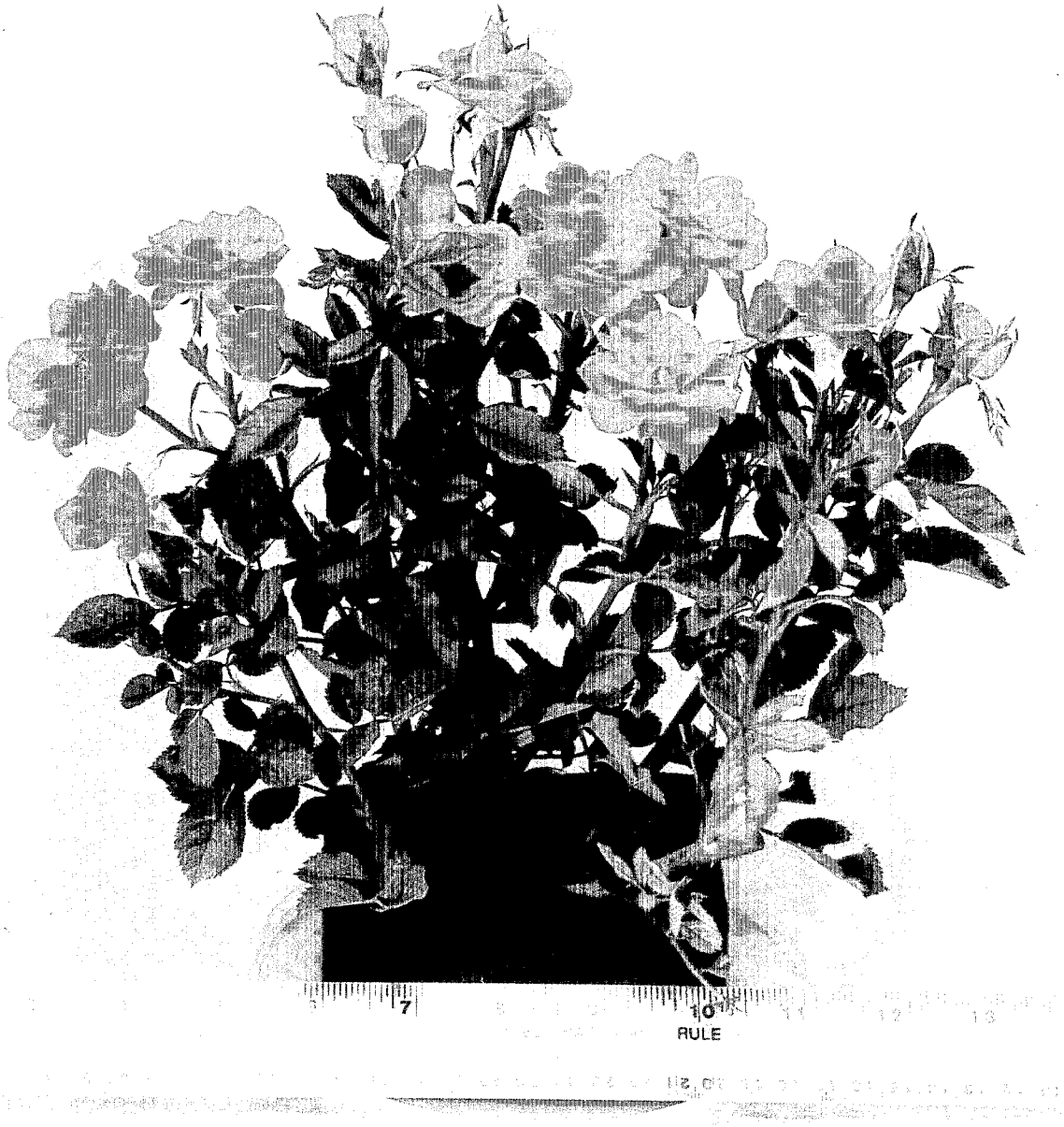
7
10
RULE

UNITED STATES PATENT AND TRADEMARK OFFICE

CERTIFICATE OF CORRECTION

PATENT NO. : Plant 9,048

DATED : January 31, 1995

INVENTOR(S) : Mogens Olesen; Pernille Olesen

It is certified that error appears in the above-indentified patent and that said Letters Patent is hereby corrected as shown below:

Column 2, line 17, change "storng" to -- strong --.

Column 3, lines 45,46, change "gnerally" to -- generally --.

Column 3, line 60, change "Pitstils" to -- Pistils --.

Column 3, line 64, change "allen closed" to -- all enclosed --.

Column 4, line 16, after "width" change "of" to -- at --.

Column 4, line 30, change "straigh" to -- straight --.

Signed and Sealed this

Twenty-sixth Day of September, 1995

*Attest:*

Bruce Lehman

BRUCE LEHMAN

*Attesting Officer*

*Commissioner of Patents and Trademarks*